United States Patent
Shelley et al.

(10) Patent No.: US 7,897,923 B2
(45) Date of Patent: *Mar. 1, 2011

(54) SAMPLE PREPARATION AND METHODS FOR PORTABLE IR SPECTROSCOPY MEASUREMENTS OF UV AND THERMAL EFFECT

(75) Inventors: Paul Shelley, Lakewood, WA (US); Greg Werner, Puyallup, WA (US)

(73) Assignee: The Boeing Company, Chicago, IL (US)

( * ) Notice: Subject to any disclaimer, the term of this patent is extended or adjusted under 35 U.S.C. 154(b) by 209 days.

This patent is subject to a terminal disclaimer.

(21) Appl. No.: 12/164,025

(22) Filed: Jun. 28, 2008

(65) Prior Publication Data

US 2009/0321648 A1    Dec. 31, 2009

(51) Int. Cl.
*G01N 21/93* (2006.01)
*G01N 21/896* (2006.01)
*G01J 3/02* (2006.01)
*G01J 5/52* (2006.01)
*G01J 3/42* (2006.01)

(52) U.S. Cl. ............ 250/339.11; 250/339.09; 250/341.8; 356/320; 356/51

(58) Field of Classification Search ............. 250/339.09, 250/339.11, 341.8; 356/302, 320, 51
See application file for complete search history.

(56) References Cited

U.S. PATENT DOCUMENTS

| | | | |
|---|---|---|---|
| 5,945,676 A * | 8/1999 | Khalil et al. ............. | 250/339.12 |
| 6,784,431 B2 | 8/2004 | Shelley et al. | |
| 6,794,651 B2 | 9/2004 | Shelley et al. | |
| 6,903,339 B2 | 6/2005 | Shelley et al. | |
| 6,906,327 B2 | 6/2005 | Shelley et al. | |
| 7,115,869 B2 | 10/2006 | Shelley et al. | |
| 7,223,977 B2 | 5/2007 | Shelley et al. | |
| 2002/0109093 A1 * | 8/2002 | Kelley ..................... | 250/339.09 |
| 2002/0113212 A1 * | 8/2002 | Meglen et al. ........... | 250/339.05 |
| 2004/0155190 A1 * | 8/2004 | Shelley et al. .......... | 250/339.11 |
| 2004/0159789 A1 * | 8/2004 | Treado et al. ............ | 250/339.07 |

* cited by examiner

*Primary Examiner* — David P Porta
*Assistant Examiner* — Jessica L Eley
(74) *Attorney, Agent, or Firm* — Tung & Associates (57) ABSTRACT

A method of non-destructively determining the physical property of a material surface, the method including irradiating a surface with infrared energy over a spectrum of wavelengths; detecting said infrared energy reflected from said surface over said spectrum of wavelengths; performing multivariate calibration of said reflected infrared energy at a plurality of selected wavelengths including said spectrum of wavelengths; using results of said multivariate calibration to predict one or more physical properties of said model material; and, determining said one or more physical properties of said surface. Details are included for the case where unidirectional fiber CFRP materials are to be calibrated and predicted because special care must be taken for that material to insure the incident light from the spectrometer is at the proper orientation for calibration and for prediction of samples in question.

20 Claims, 4 Drawing Sheets

SAMPLE PREPARATION AND METHODS FOR PORTABLE IR SPECTROSCOPY MEASUREMENTS OF UV AND THERMAL EFFECT

CROSS REFERENCE TO RELATED APPLICATIONS

This application is related to co-pending U.S. patent application Ser. Nos. 12/164,026, and 12/164,023; and 12/164,022; and 12/164,017, all filed concurrently herewith on Jun. 28, 2008, each of which applications is incorporated by reference herein in its entirety.

FIELD OF THE INVENTION

This disclosure generally relates to Infrared (IR) measurement methods, apparatus, methods for sample preparation and sample measurement methods for hand-held IR spectroscopy measurement devices for performing non-destructive IR spectroscopy measurements of surface characteristics of materials including evaluation of the condition of resin-fiber composite materials.

BACKGROUND OF THE INVENTION

IR spectroscopy measurements may be useful for a variety of purposes including aerospace, automotive and industrial applications, as well as biological and bio-medical applications. For example, infrared (IR) radiation is readily absorbed by materials in association with relative motions (vibrations) of atoms such as carbon, hydrogen, oxygen and nitrogen. As such, IR spectroscopy measurements may indicate a condition of a wide variety or organic as well as inorganic materials. For example, organic polymer materials such as resin-fiber composites may degrade over time due to a variety of reasons including heat or ultraviolet (UV) light exposure. Chemical degradation to a polymer structure may occur, thereby affecting the desired properties of the polymer structure including structural integrity such as strength of a composite or the adhesive properties of an adhesive. Near IR (1600-2400 nm) works well in testing thermal effect on resin rich materials but does not currently work on UV effect measurement. Only FT-IR (2.5 to 16.7 microns or 4000 to 600 wave numbers) works on UV effect and only FT-IR works on resin poor and fiber rich situations as in a composite repair where material is sanded away to leave a fiber rich resin poor surface.

Chemical degradation of a polymer material may be caused by exposure to normal environmental conditions over time, including normal temperature variations and ultra-violet light, as well as exposure to abnormal conditions such as elevated temperatures and stresses, resulting in oxidation and the breaking of existing polymer chemical bonds or forming of new polymer chemical bonds. Maintenance of polymeric materials requires a determination of the degree of degradation of the desirable properties, such as strength, of the polymeric material.

One non-destructive method of ascertaining the condition of polymeric containing material, such as the degree of heat effect to composite materials includes IR spectroscopy of the composite material as outlined in U.S. Pat. No. 7,113,869, which is hereby incorporated by reference in its entirety.

Other non-destructive methods in the prior art include using IR spectroscopy to determine the amount of a chromated conversion coating on a metallic substrate (U.S. Pat. No. 6,794,631), determining the amount of an anodize coating on a metallic substrate, (U.S. Pat. No. 6,784,431), determining and amount of opaque coating on a substrate (U.S. Pat. No. 6,903,339), and determining an amount of heat exposure to a resin-fiber composite substrate (U.S. Pat. No. 7,113,869), all of which are fully incorporated by reference herein.

However, in many cases, materials that could benefit from non-destructive IR spectroscopy, cannot be efficiently accessed within their normally existing operating environments by IR spectroscopy measurement methods and devices of the prior art, such as aircraft materials and parts where they must be accessed in the field by maintenance personnel to determine the acceptability of materials and parts and to aid in the repair of materials and parts. Prior methods used single absorbance band or dual absorbance bands methods and multivariate calibration with a broad band IR spectra make use of many absorbance bands and give more robust calibration and prediction results for composite material properties. Multivariate methods require careful sample preparation and in some cases proper sample fiber orientation for reproducible results with hand-held IR methods.

Thus, there is a continuing need for improved IR non-destructive testing devices and methods for performing IR spectroscopy measurements to non-destructively determine a physical property of surfaces of materials including composite fiber-resin materials.

Therefore it is an object of the disclosure to provide improved IR non-destructive testing devices and methods and to provide important sample preparation and sample orientation methods for performing IR spectroscopy measurements to non-destructively determine a physical property of surfaces of materials including composite fiber-resin materials present in operating configurations in the field, such as on aircraft.

SUMMARY OF THE INVENTION

In one embodiment a method of non-destructively determining the physical property of a material surface is provided. An illustrative embodiment of the method includes providing a series of composite material standards with increasing thermal exposure (with or without a surfacing film), irradiating the composite material standards and/or the surfacing films with mid-spectrum infrared energy, detecting infrared energy reflected from the composite material standards/surfacing films, performing multivariate calibration on the series of the infrared spectra reflected from the composite material standards/surfacing films, performing a multivariate calibration to the infrared spectra from the standards to make a model of the spectral changes with increasing thermal exposure (or decreasing mechanical properties), and using the multivariate model to predict the thermal exposure or mechanical properties of composite materials in question. The measurements described above work fine on fabric weave composite surfaces and on composite surfaces with opaque epoxy surface materials but on composite tape materials (uni-directional fibers), they do not work unless the IR light beam out of the spectrometer is properly aligned with the fiber direction of the composite tape material. This includes the case where a composite repair is in progress and one needs to read the sanded fiber rich surface to see if all non-conforming material is removed. The light beam incident upon the sample must be perpendicular to the fiber direction for good results. Surface reflectivity of calibration samples and samples in question need to be matched for best results. Glossy calibration samples will usually not give good multivariate prediction results with matte finish samples in question. Resin rich calibration samples will not give good prediction results for resin poor samples in question.

These and other objects, aspects and features of the invention will be better understood from a detailed description of the preferred embodiments of the invention which are further described below in conjunction with the accompanying Figures.

DETAILED DESCRIPTION OF THE PREFERRED EMBODIMENT

The present invention achieves the foregoing objects, aspects and features by providing a method of non-destructively determining the physical property of a material surface where the method may be accomplished by making an IR spectroscopy measurement with a portable IR measurement spectrometer including determining a strength of a composite fiber-resin material, including on an aircraft part in the field. In the case of UV light damage, the method can be used to determine the paint adhesion properties of the surface being tested.

It will be appreciated that although the invention is particularly explained with reference to using IR spectroscopy to determine a degree of heat or UV exposure effect to composite materials used in portions of aircraft, that the invention may additionally be advantageously used to determine of heat or UV exposure effect of polymer material surfaces in general.

Figure 1A:
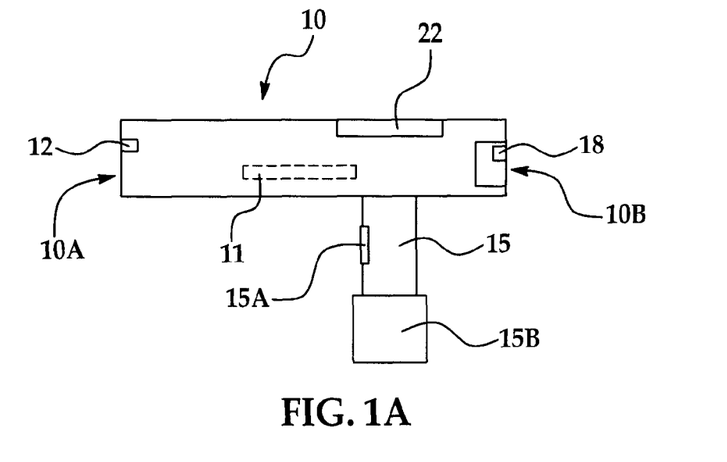
FIGS. 1A-1E are schematic diagrams of portions of a handheld portable IR spectrometer according to an embodiment of the invention.

Referring to FIG. 1A is shown a side view of a portable (handheld) IR spectrometer 10 according to an embodiment of the invention. The portable IR spectrometer 10 preferably has the capability to perform reflectance measurements, including diffuse reflectance and/or specular reflectance measurements, including diffuse-specular reflectance measurements (also referred to as an external reflectance measurement). For example, in Fourier Transform infrared portable (FT-IR) devices an IR beam is supplied to a sample at a predetermined incident angle between about 30 to about 60 degrees, most preferably 45 degrees, and reflected light from the sample is collected through a broad range of angles including the incident angle. For near IR portable devices, reflected light equal to the incident angle may not collected, and is therefore solely a diffuse reflectance measurement.

In some embodiments, the portable IR spectrometer 10 shown in FIG. 1A may be capable of performing FT-IR or near-IR spectroscopy measurements, and in one embodiment is preferably capable of performing near-IR spectroscopy measurements operating over a wavelength range of about 1600 nanometers to about 2400 nanometers. In another embodiment the wavelength range is 2.5 to 16.7 microns (or 4000 to 600 wave numbers) or the mid-IR range.

The portable IR spectrometer 10 also preferably includes a microprocessor and memory (e.g. micro-processor board 11) and may be interfaced (placed in communicated with) with other computing devices (e.g., USB port 18). The portable IR spectrometer 10 may be supplied power by one or more batteries (e.g., 13B in handle portion 13). The portable IR spectrometer 10 is preferably programmable and/or capable of accepting, storing, and executing preprogrammed instructions for carrying out IR spectroscopy measurements. The portable IR spectrometer 10 preferably has the capability to provide incident IR light (energy) and collect reflected IR spectra (e.g., through one or more IR transparent energy windows e.g., 12) over an operating wavelength range (e.g., 1600 nanometers to about 2400 nanometers or 2.5 to 16.7 microns) and to store the spectra and perform mathematical manipulation of the data comprising the spectra including multivariate analysis of the spectra. Multivariate calibration is normally performed on an external computer. The portable IR spectrometer 10 may include a triggering device e.g. 13A on handle portion 13 for triggering an IR spectroscopy measurement or the IR spectroscopy measurement may be alternately triggered by softkeys on an interactive LCD touchscreen 22. It will be appreciated that the portable IR spectrometer 10 may be of any suitable ergonomic shape to enhance the portability and ease of holding and manipulating the spectrometer to carryout field IR spectroscopy measurements.

Figure 1B:
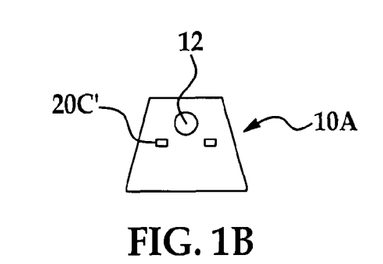
Figure 1C:
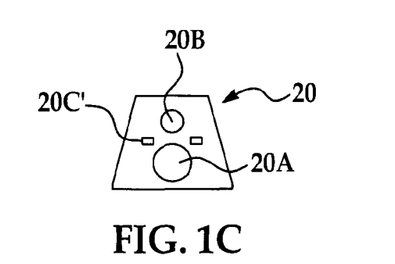

Referring to FIG. 1B, showing the front portion 10A of portable IR spectrometer 10, where IR energy may be supplied or collected through one or more IR transparent windows, e.g., shown here as a single window 12. It will be appreciated that the front portion may be of any suitable shape to enhance signal delivery and collection and calibration functions. The front portion may include aligning and/or magnetic slots 20C' or accepting and aligning calibration plate 20 (FIG. 1C). Suitable means for measuring an intensity of the reflected IR energy may include photodiodes, avalanche photodiodes, laser diodes; charge couple device (CCD) detectors, silicon detectors, or any combination thereof.

Referring to FIG. 1C the IR spectrometer 10, may include a calibration plate 20 including background reference standard material 20A and wavelength reference standard material 20B for calibrating the IR spectrometer 10 as further explained below, and aligning and/or magnetic portions 20C for aligning the calibration plate 20 and associated reference standards with the front portion 10A and IR window 12 of the IR spectrometer 10. It will be appreciated that the calibration plate 20 including associated reference standards may be of any suitable shape to enhance calibration functions.

Figure 1D:
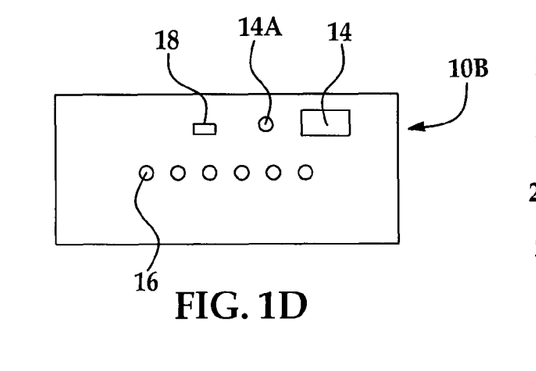

Referring to FIG. 1D is shown an exemplary back portion 10B of IR spectrometer 10, which may include an on/off power switch 14, power indicator LED 14A, USB port 18, and IR spectroscopy measurement status indicator LED lights e.g., 16. It will be appreciated that power switches and LED indicators may be placed anywhere preferably in an area that enhances manipulation and visibility by the operator including without movement of the IR spectrometer 10 from a measurement position. The hand-held IR spectrometer has to include an indication of reflected light level at the detector to allow alignment of the system so its incident IR beam is perpendicular to the fiber direction on uni-directional fiber composite materials.

Figure 1E:
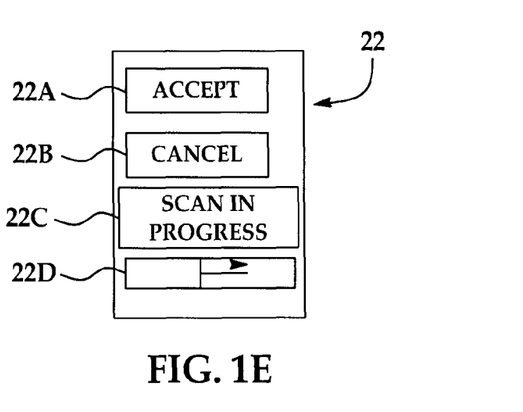

Referring to FIG. 1E, the IR spectrometer 10 may include an interactive LCD touchscreen 22 (including softkeys 22A and 22B) as well as an interactive instruction/status text display 22C and/or a status/progress bar 22D. It will be appreciated that additional softkeys and or displays may be included in order to interactively guide an operator through a desired IR spectroscopy measurement sequence including accepting or canceling IR spectroscopy measurements including calibration IR spectroscopy measurements.

The portable IR spectrometer 10, or another IR spectrometer used to make an IR spectroscopy measurement according to embodiments of the present invention, preferably has the ability to send spectra to an external computer for multivariate calibration and also can accept multivariate calibration models for use in predicting properties of samples in question. This is typically done in an external computer and the calibration method generated in the external computer is typically down loaded to the hand held device with a calibration to the proper units so the hand held device can read out thermal or UV effect in easy to understand terms like Kilojoules per meter squared for UV effect and one hour temperature equivalent for thermal effect (475 F at 1 hour for example).

There are many suitable multivariate techniques that may be used to make an IR spectroscopy measurement according to the present invention including, but not limited to, quantification methodologies, such as, partial least squares, principal component regression ("PCR"), linear regression, multiple linear regression, stepwise linear regression, ridge regression, radial basis functions, and the like.

In addition, suitable multivariant statistical approaches include classification methodologies, such as, linear discriminant analysis ("LDA"), cluster analysis (e.g., k-means, C-means, etc., both fuzzy and hard), and neural network ("NN") analysis.

Further, it will be appreciated that there are a multitude of data processing methods that may be suitably used in connection with suitable multivariant statistical approaches including spectral smoothing, first and second derivatives, normalization, multiplicative scatter corrections, and peak enhancement methods.

For example, multivariant calibration of collected IR spectra may include the selection and clustering together of groups of wavelengths on which to perform a regression analysis to determine a corresponding change in absorbance and/or reflectance. In addition, the wavelengths may be selected following taking of first and second derivatives, smoothing, and/or peak enhancement.

In addition, the multivariant calibration process may include collecting background IR spectra (including calculated absorbance and/or reflectance) which may serve as a baseline from which to analyze measurement sample IR spectra including subtracting the background spectra from the collected spectra. In addition, various processing methods as are known in the art may be used to form a single spectrum from a collect a number of collected spectra, including various averaging techniques.

In one embodiment, an IR spectrometer used to carry out an IR spectroscopy measurement according to the present invention, such as the portable IR spectrometer 10, may be provided and have stored in memory one or more background IR spectra for use in a subsequent IR spectroscopy measurement and multivariate analysis process where the background IR spectra is with respect to material in a similar condition to an area of the sample with a known level (e.g. baseline), of a physical property to be determined including an absence of the physical property. In addition, a previously determined correlation of model IR spectra (e.g., including absorbance and/or reflectance spectra) with model samples having a known level of the physical property to be determined may be stored in memory within the portable IR spectrometer 10 to perform a comparison with measured IR spectra taken from an actual sample. For example, a level of the physical property may be determined and stored or output by IR spectrometer used to make the measurement, such as the IR spectrometer 10, or a pass/fail type determination and resulting indication may stored or output. Typically the physical property of interest like $Kj/m^2$ for UV effect is used as the Y-block variable set for calibration of the IR spectra with the multivariate analysis routine. IR spectra are measured on a series of samples with increasing levels of known UV effect for the calibration.

The background IR spectra may be periodically collected by performing a background scan of a sample reference standard material according to pre-programmed instructions together with interactive operator operation of a measurement IR spectrometer, such as the portable IR spectrometer 10. The term background scan refers to a process to collect background IR spectra for use in a subsequent IR spectroscopy measurement and a subsequent multivariate analysis process where the reference standard material is in a similar condition to an area of the sample to be actually measured, but without a known level including absence of the material property to be determined, such as heat and/or UV effect to a composite material.

In one embodiment, the sample to be measured may be an aircraft, for example, present in the field such as an aircraft maintenance area, where the sample to be measured includes externally accessible aircraft portions made of a composite material, such as a fiber-resin composite material including Carbon Fiber Reinforced Plastic (CFRP).

Background reference spectra may be previously collected and stored in memory of an IR measurement spectrometer, and/or reference standard samples may be provided from which to collect a reference scan that represent different baseline reference conditions of the sample, e.g., Carbon Fiber Reinforced Plastic (CFRP) without effect from heat or UV exposure being present. FYI background materials are spectralon for near IR and diffuse (sintered) gold for mid IR hand held spectrometers and NOT reference standards with zero UV or thermal effect. Background spectra are used to calculate absorbance spectra on reference materials with known amounts of UV or thermal effect. For example, it will be appreciated that there may be a wide variety of conditions of the CFRP that may affect the IR spectra being collected, but where the physical property to be determined is absent or at a known level e.g., where the physical property to be determined is heat induced or UV induced effect to the CRFP as determined by a previously determined correlation between model IR spectra of model samples and one or more material properties of the CFRP, such as strength.

An IR measurement spectrometer, such as the portable IR spectrometer 10 may be provided with pre-programmed menus and associated preprogrammed instructions that interactively instruct (in response to operator action) an operator through an IR spectroscopy measurement sequence in connection with a desired IR non-destructive test application, which may include an aircraft maintenance procedure.

Figure 3:
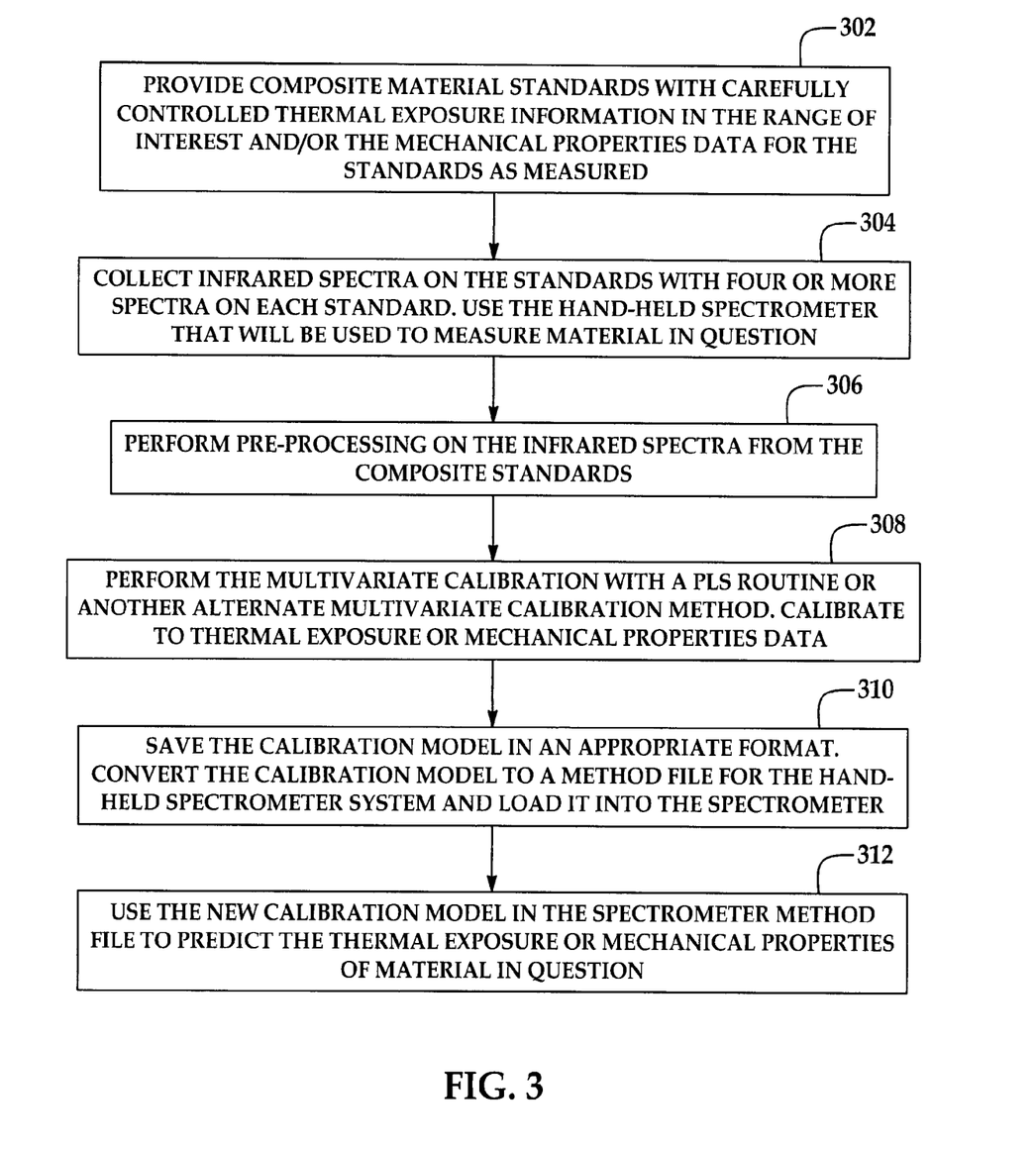
FIG. 3 is an exemplary process flow diagram for performing an IR spectroscopy measurement to determine a physical property of a sample according to an embodiment of the invention.

For example, Referring to FIG. 3 in association with FIGS. 1A-1E is shown an exemplary sequence of steps to carry out an exemplary IR non-destructive test of a composite material aircraft portion where heat and/or UV effect to the composite material may be determined by the IR spectroscopy measurement according to a pass/fail type test e.g., to be below an acceptable threshold (acceptable) or above an acceptable threshold (unacceptable).

Figure 2:
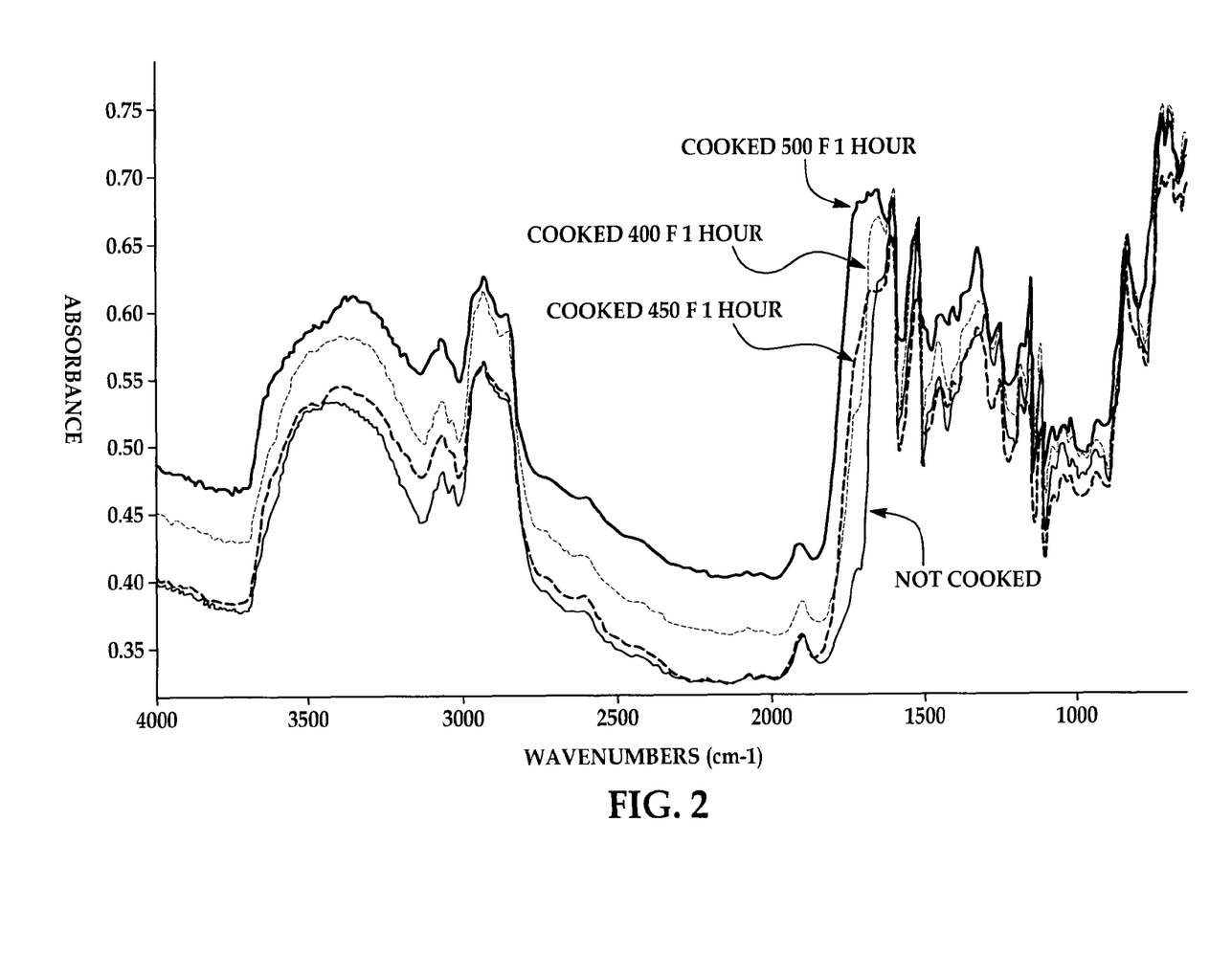
FIG. 2 is an exemplary IR spectrum showing progressive IR spectra changes according to progressive heat effect to an exemplary composite material according to an embodiment of the invention.

Referring to FIG. 2 is shown exemplary reflectance IR spectra, A, B, and C, including calculated Absorbance versus wavenumbers (cm-1) e.g., over the mid-IR range of 4000 to about 650 wavenumbers (cm-1) collected at different time periods showing progressive relative IR spectra changes in response to progressive heat effect in a composite resin-fiber material. According to the present invention, the IR wavelength range of the measuring spectrometer preferably includes the wavelength spectrum 700 to about 2400 nanometers (0.7 to 2.4 microns), and preferably, at least 1600 to 2400 nanometers for near IR spectrometers. Mid-IR or FT-IR spectrometers should be 2.5 to 25 microns (4000-400 wavenumbers) and preferably 2.5 to 16.7 microns.

Referring back to FIG. 3, As shown in block 302 of flow diagram 300 in FIG. 3, the thermal effect calibration begins with CFRP standards that are carefully cooked and then tested to obtain residual mechanical properties. Block 304 shows the mid-IR spectral data collection step and the raw infrared spectra are shown in FIG. 2. Block 306 shows the data preprocessing step. Block 308 shows the multivariate calibration step. Block 310 shows the step where the multivariate calibration is saved in an appropriate format and then loaded into the hand-held mid-IR device or near-IR device that will be used to read thermal effect on CFRP material in question. Block 312 shows material in question being predicted for residual stress values that would indicate the extent of thermal effect in the material in question. If the original standards are predicted here, one can develop an accuracy figure for the methods based on the difference between the known stress numbers and those predicted by the method just developed.

Materials defined above are used for background for near IR and mid-IR, not composite materials without UV or thermal effect.

In step 304, the operator may position a reference standard sample material to collect background spectra (background scan), for example a 99% reflectance standard 20A, which may be provided on a reference plate 20 (FIG. 1C) that is positioned over an IR energy source and spectra collecting port 12 (FIG. 1B) on the front portion of the portable IR spectrometer 10. The operator may instruct the portable IR spectrometer to make a scan e.g., by pressing trigger 13A or by interactive operation with softkeys (pressing) on an LCD screen 22 to take one or more IR background spectra (scans) over a desired wavelength range. Indicating means, such as the LCD screen 22 and/or LED lights 16 (FIG. 1D) on the back of the portable IR spectrometer may indicate the progress, completion, and/or success of the measurement (IR scan). For example, if a successful background scan is indicated, the operator may indicate acceptance of the scan by pressing an interactive softkey e.g., 22A, which may cause the IR spectrometer to store the background scan for use in a subsequent IR spectroscopy measurement. It will be appreciated that multivariant analysis may be employed in the background scan process.

In step 304, following taking and storing of the background scan, a wavelength accuracy test may be made by a similar process of taking an IR scan (collecting one or more spectra) of a predetermined reference wavelength standard 20B (FIG. 1C; e.g., material having a predetermined IR spectra the same or similar to material to be measured) to complete the calibration process. Wavelength calibration is used for near IR only and is not necessary for FT-IR because a laser defines the wavelength scale and position. For example, following collecting of the wavelength standard spectra, the collected spectra may be compared to stored model IR spectra to determine whether the collected IR spectra (including absorbance and/or reflectance) corresponds to the model IR spectra within a predetermined accuracy window. It will be appreciated that multivariant analysis may be employed in the wavelength accuracy scan process. If the wavelength accuracy is determined to be within an accuracy window, the operator may be visually or audibly notified, e.g., by "pass' text being displayed on the LCD screen 22 and/or by an LED indicator light 22D. The operator may also have the option of accepting or canceling the completed scan e.g., softkeys in LCD screen 22. The operator may then proceed to step 303 if the wavelength accuracy test is passed or return to step 303A to re-start the calibration process.

In step 304, the operator may interactively select a pre-existing measurement configuration and perform a second background scan, which may be indicated (requested) on the LCD screen 22. For example, the selectable configuration may include, a sample configuration corresponding to a predetermined baseline of effect (e.g., heat and/or UV effect) which may include a different type of condition or different type of effect than the one being determined and may include a known level (including absence of) the effect to be determined. For example, the pre-existing configurations may include specific conditions of the composite material CFRP, such as painted, painted and struck by lightning, bare CFRP not abraded or sanded, sanded or abraded but not painted CFRP, and the like. The pre-existing configurations, for example, may include different multivariate calibration files for processes associated with the IR spectroscopy measurement, such as analysis of different groups of wavelengths. In step 307, following the second background scan (background spectra or spectrum collected and stored in memory) in step 305, the operator may then employ portable IR spectrometer 10 in an actual IR material inspection test in step 307. For example, an exemplary IR material inspection test may include determining whether heat and/or UV effect to a CFRP aircraft part is acceptable or unacceptable. For example, depending on the configuration of the CFRP, pre-programmed instructions may instruct the operator (e.g., LCD touchscreen 22) to take a plurality of scans of the aircraft part in order to improve a signal to noise ratio (e.g., where a portion of the CFRP may have been removed). Additionally, it has been found that an important aspect of making IR spectroscopy measurements (including calibration processes) of composite materials, is that the IR energy incident and collecting angle (i.e., the orientation of the portable IR spectrometer) should be done with a predetermined orientation with respect to the alignment of the composite material (e.g., fiber orientation direction) to obtain good quality data (spectra). This is important for uni-directional fiber composites but not needed for composite fabric materials or for opaque epoxy surface materials on CFRP. It is useful for the hand-held spectrometer to have an indicator that shows the IR power at the detector. This can be used to turn the spectrometer on the sample to maximize the IR power returning from the CFRP being measured. When the power is maximized the fiber direction is correct with respect to the spectrometer. This should be done for calibration spectra and spectra for samples in question. It is often the case that the fiber direction is NOT easy to see (bag side sample surfaces for example) and it is desirable to have the spectrometer properly oriented with respect to the sample fiber direction. This is generally not critical for woven composite materials. It is also very desirable to have the spectrometer calibrated for the proper composite surface conditions (bag-side, scarfed, tool-side, surface materials, etc all require a separate multivariate calibration because IR spectra are very sensitive to resin chemistry and surface conditions.

Figure 4A:
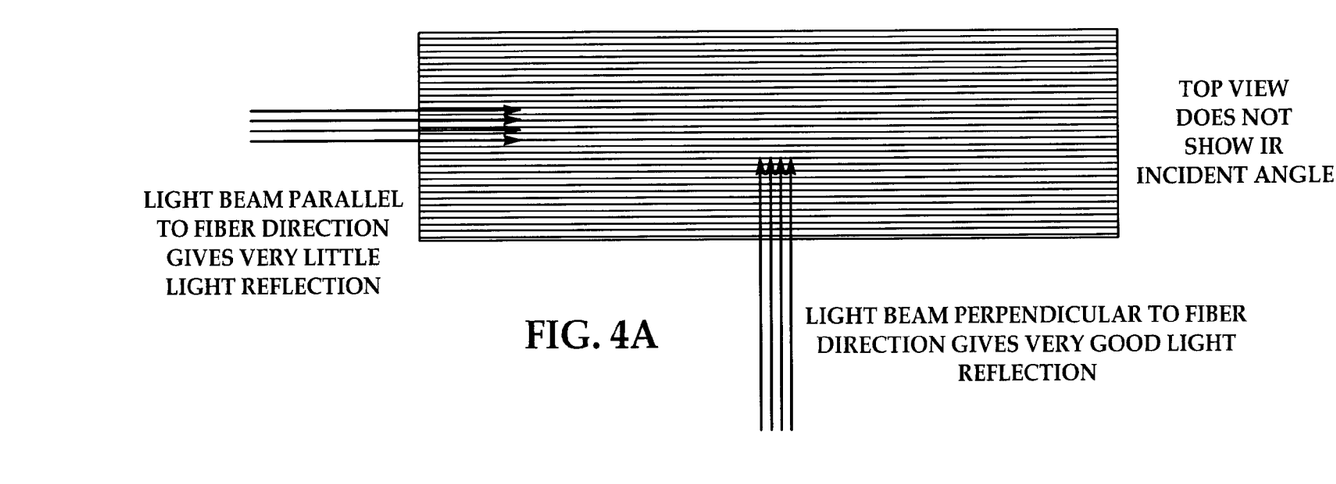
FIGS. 4A-4C are an exemplary schematic diagrams showing the IR spectroscopy measurement process with the proper light incident angle and with the wrong light incident angle and the effects on the reflected beam in both cases.
Figure 4B:
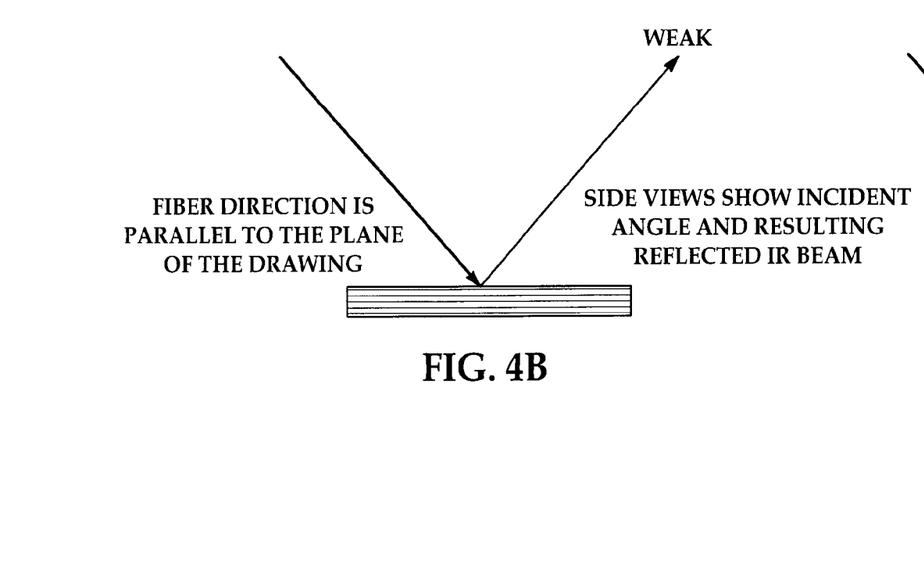
Figure 4C:
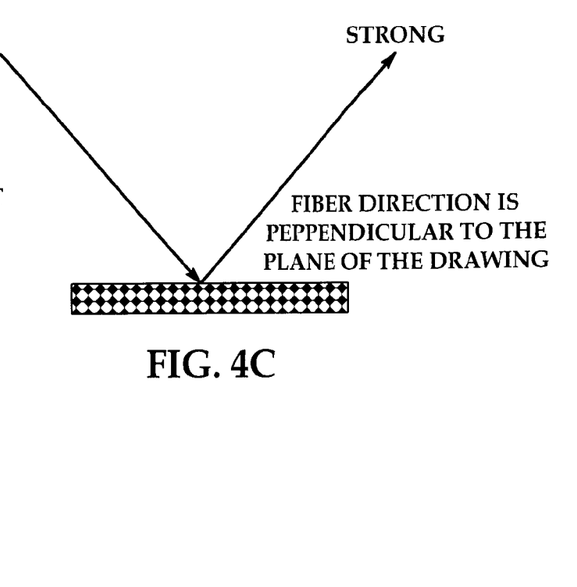

Referring now to FIG. 4, an exemplary IR spectroscopy measurement process is shown with details for the importance of making the spectrometer light beam oriented properly with respect to the graphite fiber direction in uni-directional fiber composites. FIG. 4a is a top view showing the right and wrong light beam incident directions. Only the proper incident direction (± about 10 degrees) give optimum light reflection power and insures the best quality spectra for calibration and prediction. FIGS. 4b and 4c are the side views for the wrong and right incident light directions for uni-directional CFRP tape composites.

Referring to FIG. 5, an exemplary IR spectroscopy measurement process is shown including an exemplary mapping of an affected aircraft portion 40 (e.g., heat and/or UV effect) formed of composite material. For example, following calibration steps outlined in FIG. 3, the calibration of the portable IR spectrometer 10 may be first checked (confirmed) on an unaffected portion e.g., 42 of the composite material e.g., a distance d1 (e.g. 3 inches) from the suspected heat and/or UV affected portion 44 and the portable IR spectrometer then moved successively closer to the suspected affected portion 42 from a plurality of radial extending directions e.g., 46, while making sequential IR reflectance measurements following each move according to preferred embodiments outlined above. A boundary 48 (e.g., a boundary marking transition from pass (acceptable strength) to fail (unacceptable strength) surrounding the heat and/or UV affected portion 44 may then be determined and marked according to the sequential IR reflectance measurements. Thermal effect is generally localized and the above approach works well but UV effect is generally over a very broad area and several readings are generally made in each area to verify the extent of UV effect there.

For example, the IR spectroscopy measurement process may be part of an aircraft maintenance procedure, e.g., where the affected area of the composite material is first determined and then the non-conforming material progressively removed (e.g., successive plies of a multi-ply material removed) followed by further IR spectroscopy measurement sequences until the non-conforming material is completely removed. It will be appreciated that during a sequential measurement process that new background scans may be periodically required depending on preprogrammed criteria where changed measurement conditions are detected.

While the embodiments illustrated in the Figures and described above are presently preferred, it should be understood that these embodiments are offered by way of example only. The invention is not limited to a particular embodiment, but extends to various modifications, combinations, and permutations as will occur to the ordinarily skilled artisan that nevertheless fall within the scope of the appended claims.

What is claimed is:

1. A method of non-destructively determining the physical property of a material surface comprising:
    irradiating a surface with infrared energy over a spectrum of wavelengths by a hand-held portable IR spectrometer;
    said hand-held portable IR spectrometer comprises an accessory calibration plate attachable over an IR signal collection port wherein said calibration plate comprises a reference sample comprising a condition approximating an actual sample wherein said physical property is present at a predetermined level;
    detecting said infrared energy reflected from said surface over said spectrum of wavelengths;
    performing multivariate analysis of said reflected infrared energy at a plurality of selected wavelengths comprising said spectrum of wavelengths;
    comparing results of said multivariate analysis with a predetermined correlation between model infrared energy spectra comprising said spectrum of wavelengths and a model material surface, said predetermined correlation with said model material surface comprising one or more physical properties of said model material; and,
    determining said one or more physical properties of said surface.

2. The method of claim 1, wherein said multivariant analysis comprises multivariant statistical approaches to determine absorbance and/or reflectance values at selected groups of wavelengths comprising said spectrum of wavelengths.

3. The method of claim 1, wherein said surface comprises a composite resin-fiber material.

4. The method of claims 3, wherein said material property comprises strength of said resin-fiber material.

5. The method of claim 1, wherein said step of irradiating a surface is preceded by a calibration process comprising collecting background spectra over said spectrum of wavelengths from a reference sample wherein said physical property is present at a predetermined level.

6. The method of claim 1, wherein said step of irradiating a surface is preceded by a calibration process comprising collecting reference spectra over said spectrum of wavelengths from a reference sample comprising a predetermined IR spectroscopy measurement spectrum.

7. The method of claim 1, wherein said spectrum of wavelengths is from about 1600 to about 2400 nanometers.

8. The method of claim 1, wherein said hand-held portable IR spectrometer detects said infrared energy reflected according one of a diffuse reflectance measurement and a diffuse-specular measurement.

9. The method of claim 1, wherein said hand-held portable IR spectrometer comprises an interactive LCD display to display programmable visual menus and/or display status of the hand-held portable IR spectrometer and/or an IR spectroscopy measurement.

10. The method of claim 1, wherein said hand-held portable IR spectrometer comprises LED indicators to indicate a status of the hand-held portable IR spectrometer and/or an IR spectroscopy measurement.

11. The method of claim 1, wherein said hand-held portable IR spectrometer comprises a processor to execute and memory to store preprogrammed instructions.

12. The method of claim 1, wherein said hand-held portable IR spectrometer is adapted to display a sequence of operator instructions and menus to accomplish a sequence of steps in a pre-programmed IR spectroscopy measurement process.

13. A method of non-destructively determining a strength of heat and/or UV affected polymer composite material comprising:
    irradiating a polymer composite material surface with infrared energy over a spectrum of wavelengths by a hand-held portable IR spectrometer;
    said hand-held portable IR spectrometer comprises an accessory calibration plate attachable over an IR signal collection port wherein said calibration late comprises a reference sample comprising a condition approximating an actual sample wherein said physical property is present at a predetermined level;
    detecting said infrared energy reflected from said polymer composite material surface over said spectrum of wavelengths;
    performing multivariate analysis of said reflected infrared energy at a plurality of selected wavelengths comprising said spectrum of wavelengths;

comparing results of said multivariate analysis with a predetermined correlation between model infrared energy spectra comprising said spectrum of wavelengths and a model polymer composite material, said predetermined correlation with said model composite material comprising a strength of said polymer composite material correlated with changes in said model infrared energy spectra associated with ultraviolet and/or heat induced effect to said polymer composite material; and, determining said strength of said polymer composite material surface.

14. A hand-held portable IR spectrometer comprising:

an infrared energy source adapted to irradiate a surface with infrared energy over a spectrum of wavelengths;

wherein said hand-held portable IR spectrometer comprises an accessory calibration plate attachable over an IR signal collection port wherein said calibration plate comprises a reference sample comprising a predetermined absorbance and/or reflectance spectrum;

an infrared energy detector adapted to detect said infrared energy reflected from said surface over said spectrum of wavelengths;

wherein said hand-held portable IR spectrometer is adapted to perform multivariate analysis of said reflected infrared energy at a plurality of selected wavelengths comprising said spectrum of wavelengths; and, wherein said hand-held portable IR spectrometer is adapted to compare results of said multivariate analysis with a predetermined correlation between model infrared energy spectra comprising said spectrum of wavelengths and a model material surface, said predetermined correlation with said model material surface comprising one or more physical properties of said model material, said comparison to determine said one or more physical properties of said surface.

15. The portable IR spectrometer of claim 14, wherein said hand-held portable IR spectrometer is adapted to determine absorbance and/or reflectance values at selected groups of wavelengths comprising said spectrum of wavelengths.

16. The portable IR spectrometer of claim 14, wherein said spectrum of wavelengths is from about 700 to about 2400 nanometers.

17. The portable IR spectrometer of claim 14, wherein said hand-held portable IR spectrometer is adapted to detect said infrared energy reflected according one of a diffuse reflectance measurement and a diffuse-specular measurement.

18. The portable IR spectrometer of claim 14, wherein said hand-held portable IR spectrometer comprises an interactive LCD display to display programmable visual menus and/or display a status of the hand-held portable IR spectrometer and/or an IR spectroscopy measurement.

19. The portable IR spectrometer of claim 14, wherein said hand-held portable IR spectrometer comprises LED indicators to indicate a status of the hand-held portable IR spectrometer and/or an IR spectroscopy measurement.

20. The portable IR spectrometer of claim 14, wherein said hand-held portable IR spectrometer is adapted to display a sequence of operator instructions and menus to accomplish a sequence of steps in a pre-programmed IR spectroscopy measurement process.

* * * * *